United States Patent [19]
Dave et al.

[11] Patent Number: 5,831,099
[45] Date of Patent: Nov. 3, 1998

[54] COMPOUNDS OF 1,5-DISUBSTITUTED-3,7 DIAZA BICYCLO [3.3.0] OCTANES AND PRODUCTS CONTAINING THE SAME

[75] Inventors: Paritosh R. Dave, Bridgewater; Theodore Axenrod, Englewood Cliffs; Farhad Forohar, Flanders, all of N.J.

[73] Assignee: The United States of America as represented by the Secretary of the Army, Washington, D.C.

[21] Appl. No.: 54,312

[22] Filed: Mar. 31, 1998

Related U.S. Application Data

[63] Continuation of Ser. No. 402,273, Mar. 10, 1995, abandoned.

[51] Int. Cl.$^6$ .................................................. C07D 487/04

[52] U.S. Cl. ............................................................. 548/453

[58] Field of Search ............................................... 548/453

[56] References Cited

PUBLICATIONS

Dave et al., J. Org. Chem., 61(25), 8897–8903 (1996).
Ammon et al., Acta Crystallogr., Sect. B: Struct. Sci., B52(2), 352–6 (1996).

*Primary Examiner*—Johann Richter
*Assistant Examiner*—Laura R.C. Lutz
*Attorney, Agent, or Firm*—John Moran; John Callaghan

[57] ABSTRACT

Overall, the invention provides the chemistry for the compounds and for the processes to prepare compounds derived from 1,5-diazacyclooctanes. This makes available high density, high melting point, thermally stable small and medium ring nitrogen heterocycles that may also contain N-nitro, C-nitro or other functional groups. The compounds include cyclooctanes, bicyclo octanes, propellanes and functionalized derivatives of the above compounds. The preparations can include transannular cyclizations. The materials have several applications; e.g., the polynitro compounds are energetic materials.

1 Claim, 6 Drawing Sheets

Figure 1A

SYNTHESIS OF N,N'-DITOSYL-1,5-DINITRO-3,7-DIAZABICYCLOOCTANE

Figure 1B

SYNTHESIS OF
1,3,5,7-TETRANITRO-3,7-DIAZABICYCLOOCTANE

Figure IC

REDUCTION OF 3,7-BISMETHYLENE-1,5-DIAZACYCLOOCTANE

PROPELLANE NMR DATA

| $\delta\,^1H$ | $\delta\,^1H$ | $\delta\,^1H$ |
|---|---|---|
| 2.45 | 2.45 | 2.41 |
| 3.62 CH$_2$O | 2.73 CH$_2$S | -------- |
| 3.01 | 3.01 | |
| 2.95 CH$_2$N (J$_{AB}$ = 9.5Hz) | 2.96 CH$_2$N (J$_{AB}$ = 9.5Hz) | 2.99 |
| 7.32 | 7.32 | 7.28 |
| 7.35 | 7.35 | 7.31 |
| 7.58 | 7.57 | 7.50 |
| 7.61 | 7.60 | 7.53 |

| $\delta\,^{13}C$ | $\delta\,^{13}C$ | $\delta\,^{13}C$ |
|---|---|---|
| 21.62 | 21.61 | 21.47 |
| 76.19 CH$_2$O | 42.22 CH$_2$S | --------- |
| 56.03 CH$_2$N | 57.15 CH$_2$N | 56.08 CH$_2$N |
| 63.53 Cq | 65.88 Cq | 60.73 Cq |
| 127.95 | 127.93 | 127.70 |
| 129.99 | 129.93 | 129.92 |
| 131.05 Cq | 131.10 Cq | 130.85 Cq |
| 144.45 Cq | 144.34 Cq | 144.44 Cq |

| C$_{26}$N$_2$S$_2$O$_5$ | C$_{22}$H$_{26}$N$_2$S$_3$O$_4$ | C$_{29}$H$_{33}$N$_3$S$_3$O$_6$ |
|---|---|---|
| 462.128315 | 478.10547 | 615.1532 |
| Found CI, 463 (M+1) | Found EI, 478 | Found CI, 633 (M+18) |
| 480 (M+18) | mp 195-6 °C | mp 208-212 °C |

Figure 3B

COMPOUNDS OF 1,5-DISUBSTITUTED-3,7 DIAZA BICYCLO [3.3.0] OCTANES AND PRODUCTS CONTAINING THE SAME

STATEMENT OF RELATED APPLICATIONS

This application is a continuation of 08/402,273 filed Mar. 10, 1995, now abandoned.

STATEMENT OF GOVERNMENT INTEREST

The invention described herein may be manufactured, used and licensed by or for the United States Government for governmental purposes without the payment to us of any royalties thereon.

This application is related to the U.S. Patent Applications described below; the applications have been filed simultaneously with this application. The applications are:

DAR 36-93 Ser. No. 08/402,078, filed Mar. 10, 1995
DAR 36-93A Ser. No. 08/402,274, filed Mar. 10, 1995
DAR 36-93C Ser. No. 08/402,074, filed Mar. 10, 1995
DAR 36-93D Ser. No. 08/402,073, filed Mar. 10, 1995

BACKGROUND OF INVENTION

This invention relates to chemical compounds, processes for making the compounds and products using the compounds. Generally, cyclooctanes are used in many applications. Nitro functionalized cyclooctanes are energetic materials. Derivatives of these cyclooctanes and the bicyclo and tricyclo octanes obtained from the cyclooctanes are also used in applications such as fragrances, polymers, templates for synthetic zeolites. These are difficult to prepare and relatively few compounds are available. In particular, 3,7 disubstituted-1,5 diaza cyclooctanes that have keto substituents have not been available. The keto compounds as well as the functionalized derivatives of diaza cyclooctane and the processes for preparing the same would be worthwhile advances in the field.

SUMMARY OF INVENTION AND FIGURES

Overall, the invention provides the chemistry for the compounds and for the processes to prepare compounds derived from 1,5-diazacyclooctanes. This makes available high density, high melting point, thermally stable small and medium ring nitrogen heterocycles that may also contain N-nitro, C-nitro or other functional groups. The materials are useful in themselves and as intermediates, e.g., energetic materials, polymers, polymerization accelerators, mimics of naturally occurring biochemical structures, fragrance compositions, templates for synthesis of zeolites, metal ligands. The bicyclo diaza octanes and the [m.3.3.] propellanes have favorable stereochemistry for forming metal complexes through the aza N atoms of adjacent rings.

The present invention is directed to chemical compounds of 3,7 disubstituted-1,5 diazacyclooctanes in which the aza nitrogen atoms are substituted with carbonyl or sulfonyl groups and to processes using these compounds and to derivatives of these compounds. The amido and sulfamido substituents tend to protect the aza atoms in subsequent reactions. In this manner, the functionalization of the cyclooctane can proceed by the choice of functionalizing the ring atoms or the aza atoms or both. It provides new compounds of functionalized cyclooctanes and also bicyclic and tricylic cyclooctanes and the functionalized derivatives of the same.

A class of particular interest is the 3,7-exo( bis methylene) -1,5 diazacyclooctanes. These compounds can be oxidized to the corresponding diketo cyclooctanes. The cyclooctane compounds are especially important because they can be used as reactants in taking advantage of transannular cyclization processes for the preparation of bicyclic octanes and the functionalized bicyclic octanes. As intermediates, the functionalized cyclooctanes can be converted further to polynitro and poly(difluoroamine) cyclooctanes and the polynitro bicylo octanes, which are energetic materials. Alternatively, the bicyclic octanes can be reacted with ring closing compounds to form [m.3.3] propellanes. It should be noted that the rules of nomenclature for organic compounds change the positional assignments for the hetero compounds when the structues are cyclooctane or bicyclo octane or propellane.

The processes of this invention for preparing the 3,7-disubstituted-1,5 diaza cyclooctanes are advantageous in that the reaction conditions give improved yields and readily recoverable products. The processes of this invention are both in individual steps and in sequences of steps for overall reaction schemes. In one sequence, the disubstituted cyclooctanes are prepared and then converted to the diketo compounds. The diketo compounds are converted to oximes. The oximes are converted to the nitro substituents. Next, the aza nitrogens are converted to N-nitro groups to form the polynitro cyclooctanes. Alternatively, the oxime cyclooctane can be converted to the bicyclo octane by transannular cyclization and the bicyclic compound is nitrated to a polynitro bicyclo octane. In another sequence, the bismethylene cyclooctane is converted to the bicyclooctane by transannular cyclization. The bicyclic compound is converted to the [m.3.3.] diaza propellane. This provides a process for preparation of a cyclooctane, conversion of the cyclooctane to the bicyclic octane and converting this to the tricyclic compound.

BRIEF DESCRIPTION OF THE DRAWINGS

The Figures illustrate several aspects of the invention.

FIG. 1A is the reaction scheme for the preparation of the 3,7-disubstituted-1,5 diaza cyclooctanes and the 3,7-diketo-1,5 diaza cyclooctanes.

FIG. 1B is the continuation of the reaction scheme in which the diketo compound is functionalized to the dioxime and the dioxime is simultaneously functionalized and cyclized to the dinitrobicylooctane.

FIG. 1C is the continuation of the reaction scheme in which the dinitro bicylooctane is further functionalized to the polynitrobicyclooctane.

In FIG. 3A reactions are shown which provide heterocyclic third rings; the —O—, —S— and —N— heterocyclic propellanes are illustrated.

DETAILED DESCRIPTION OF THE INVENTTON

The practice of the invention and the compounds, processes and products of the invention are further described by reference to the following detailed description of the compounds and processes to prepare the compounds and by reference to the accompanying Figures.

FIG. 1A illustrates the compounds of and processes of preparation of the 3,7-disubstituted-1,5 diaza cyclooctanes. In particular, the 3,7-exo (bismethylene) and 3,7-diketo compounds are shown. The aza nitrogens as shown have either tosyl or methanesulfonyl substituents. Generally, the process is characterized by reacting an ethylenically unsaturated compound with an amide or sulfonamide in solution and in the presence of a base to form the cyclooctane. The ethylenically unsaturated compound has two substituents L that are both attached to one of the unsaturated carbon atoms, geminal substitution. The substituent L can be methylene with a halogen, lower alkyl carboxy, or lower alkyl sulfonyl group. It may have the same groups or different groups. Examples of the groups are chlorine, bromine, iodine, fluorine, acetate, mesylate and tosylate. The halogens are preferred Depending upon the amide or the sulfonamide, the aza nitrogen is protected with carbonyl or sulfonyl groups. In the reaction as shown, p-toluene sulfonamide or methane sulfonamide was reacted with 3-chloro-2chloromethylpropene in the presence of base, potassium carbonate, and in a solvent of acetonitrile. The 3,7-exo (bismethylene)-1,5 diazacyclooctanes were easily isolated in pure form by recrystallization and obtained in good yield. In the second step, the exo bismethylene compounds are reacted with an oxidizing agent, for example ozone, at −78° C. to give the diketo compound. This was very easily recovered in the form of crystalline needles.

For preparation of the 3,7-exo(bismethylene)-1,5-diazacyclooctane, the preferred reactant is the 3-chloro-2-chloromethyl propene. For other substituted cyclooctanes, the other ethylenically unsaturated compounds described above would be suitable.

FIG. 1B illustrates the steps of reacting the diketo compound of FIG. 1A to a dinitro bicyclooctane. In this sequence, there is a first step where the diketo form of the diazacyclooctane is functionalized through the diketo groups to corresponding oxime groups. The dioxime cyclooctane is simultaneously oxidized and caused to undergo transannular cyclization to form the 3,7-dinitro-1,5 diaza bicyclo octane. The amide or sulfonamide substituents protect the aza nitrogens during both steps of this reaction scheme. Conventional reagents for the oximation and nitration are used in the reactions and are as shown in the Figure.

FIG. 1C shows additional functionalization reaction steps for the bicyclo octane. Here, the additional functionalization is by the reaction of the diazabicyclic octane to the tetranitro bicyclo octane, 3,7-dinitro-1,5-dinitrato bicyclo octane. This functionalization step illustrates the removal of the protecting substituents from the aza nitrogen atoms and replacement of these with the desired nitro groups to obtain the functionalized bicyclo octane, which would be the desired product for use as an energetic material.

Figure 2:
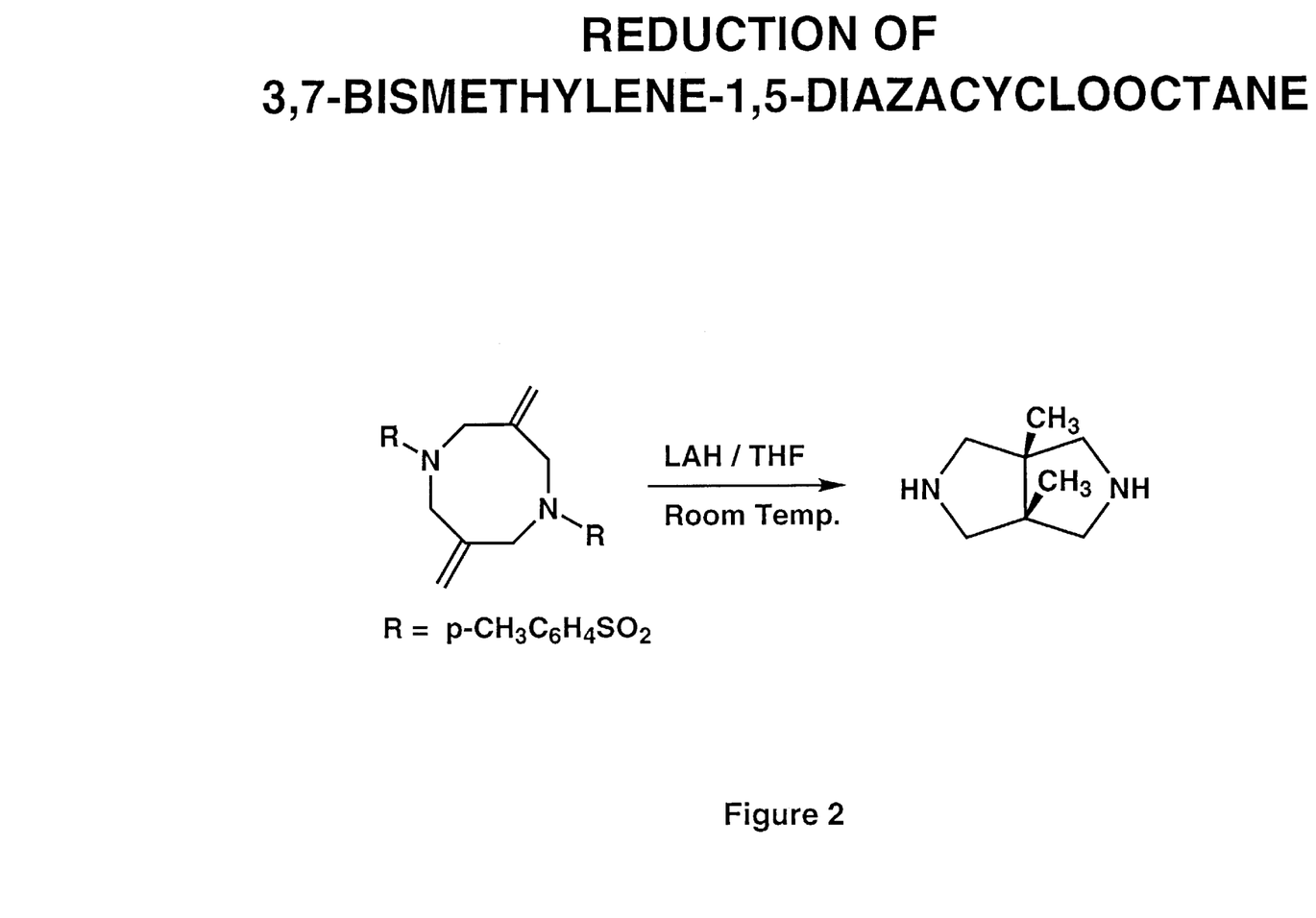
FIG. 2 illustrates the simultaneous reduction and transannular cyclization of the exo(bisalkylene)-1,5 diaza compounds.

FIG. 2 shows another of the transannular cyclization reactions in which the 3,7-disubstituted-1,5 diazacyclooctane is converted to the bicyclo octane. This is also known as a ring contraction; here, the 3,7-exo(bismethylene)-1,5 diaza cyclooctane is converted to the bicyclooctane. As shown in FIG. 2, 3,7 exo(bismethylene)-1,5 diazacyclooctane is simultaneously reduced and cyclized to the polycyclic octane, 1,5 dimethyl-3,7 diazabicyclo octane. The reaction conditions were at room temperature in a solvent, THF, and with a common reducing agent, LAH. The reduction reaction converts the aza nitrogens from the amide or sulfamide form to the amine or hydrogen substituted form. An advantage of having the aza nitrogens substituted with hydrogen is that the compound can be reacted with other functionalizing agents to obtain other desired compounds. For this reason the hydrogen substituted aza compounds have particular value as intermediates to other compounds. The hydrogen substituted variety also has the best metal complexing action of the several aza nitrogens. In this regard, the hydrogen substituted bicyclo octanes and propellanes have favorable stereochemistry to complex with metals such as platinum or to bond other metals to the octane or a substrate containing the octane.

Figure 3A:
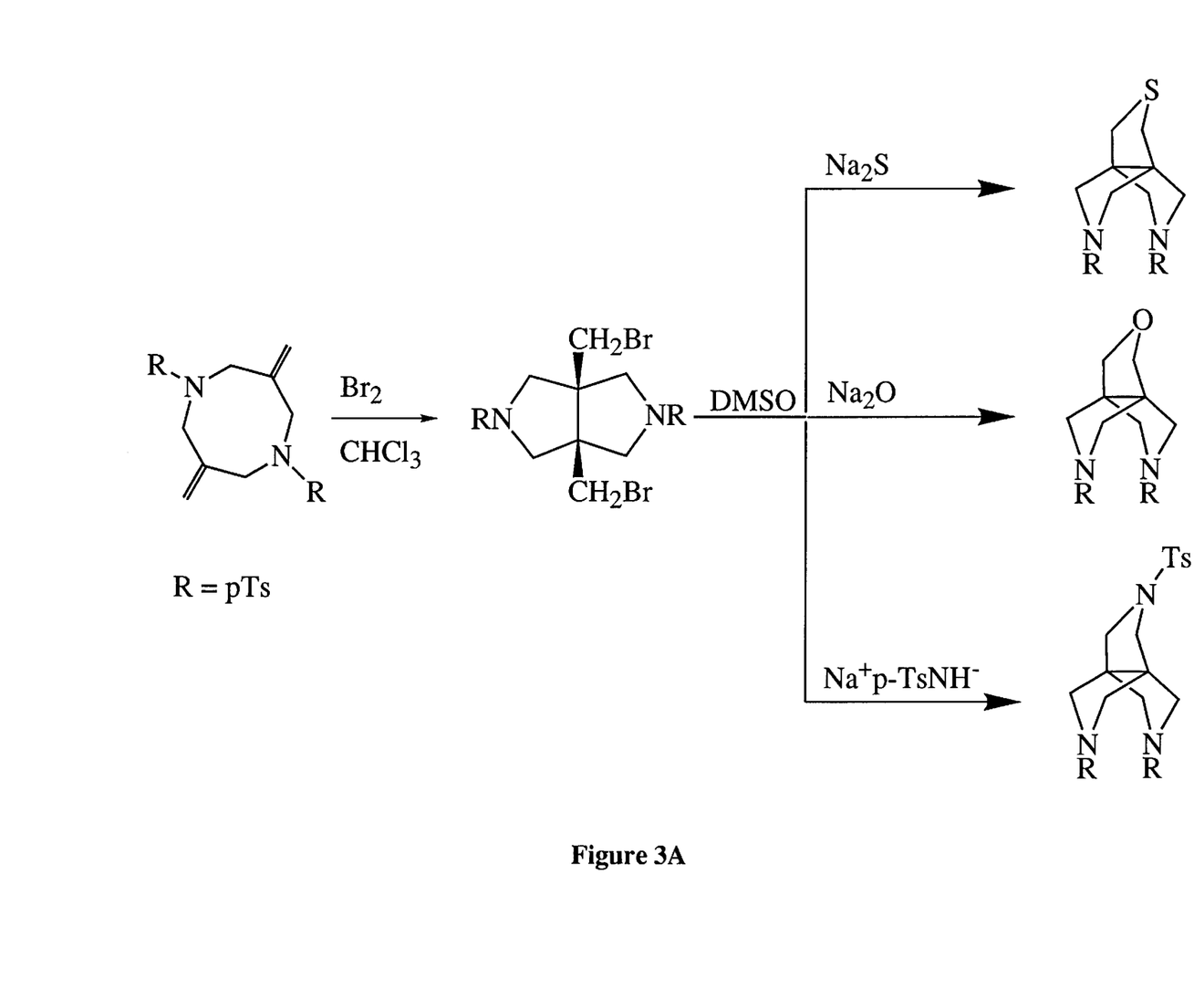
FIG. 3A illustrates the reaction scheme in which a 3,7-exo(bisalkylene)-1,5 diazacyclooctane undergoes transannular cyclization to the corresponding bicyclic octane. As a first step, the compound undergoes simultaneous alkylhalogenation and transannular cyclization to the haloalkyl bicylooctane. In the subsequent step, the bicyclic octane is then reacted with chain closing agents to form [m.3.3.] propellanes. When m is at least 3, the third ring will have from 5 to about 9 atoms. It can be either a carbocycle or a heterocycle.

FIG. 3A illustrates the conversion of the 3,7-disubstituted-1,5 diaza cyclooctanes to the bicyclic octanes and then to the [m.3.3.] propellanes. The reaction scheme here is shown as beginning with the 3,7-exo(bismethylene)-1,5 diazacylooctane. The first step is the simultaneous halogenation and transannular cyclization to form the 3,7-dihaloalkyl-1,5 diaza bicyclo octane. The reaction was conducted in a solvent and used bromine for the halogenation. As a second step, the bicyclic octane is reacted with a ring closing compound to form the [m.3.3.] propellane. The propellane may have a third ring that is a carbocycle or a heterocycle. Usually, the third ring will have from 5 to about 9 atoms. The longer rings tend to cause entropic factors in forming the propellane compound. The hetero atom may be N, S or O. A five membered ring would be symmetric with the other two aza nitrogen rings. It can be appreciated that the adjacent rings with aza nitrogen are the same nitrogen atom structure as is in Cis Platin. The compounds would have similar properties. The propellanes may be functionalized by nitration to form the polynitro derivatives which can be used as energetic materials.

The functionalization of compounds as used in this invention includes the functionalization of the cyclooctanes, bicyclo octanes and propellanes. It is generally placing on a compound a group with desired properties. The preferred such groups include but are not limited to: nitro, organosulfonyl, organocarbonyl, substituted or unsubstituted amino, alkyl and aryl groups. As pointed out above, the functionalization proceeds by replacing an existing substituent with a more desired substituent. The functionalization can be either immediate or intermediate. For example, because of the protective effect for aza nitrogen, a tosyl group is attached to the aza nitrogen and carried as long as possible until it is no longer needed and is replaced with a more desired group. This may be at the reaction step in which the ultimate product is desired.

Particular compounds and specific processes for illustrating the invention are shown in the following examples. The example on oxidation of the 1,5-di(p-toluenesulfonamido) diazacyclooctane-3,7-diols is presented for comparison purposes. Additional information on experimental procedures for practicing the invention is incorporated by reference from the publication "1,5 Diazacyclooctane-3,7-Derivatives, . . . ", Tetrahedron Letters, Vol. #5, No. 478. pps. 8965–8968, 1994.

1,5-Di(methanesulfonamido)diazacyclooctane-3,7-dione (2b)

A mixture of ozone in oxygen was bubbled through a suspension of N,N'-dimethanesulfonyl-3,7-dimethyleneoctahydro-1,5-diazocine (1.0 g, 3.34 mmol) in methylene chloride (50 mL) at −78° C. until the blue color of ozone persisted. The mixture was stirred for an hour and then allowed to warm to 0° C. Oxygen was then bubbled through the reaction mixture to remove excess ozone. Excess dimethyl sulfide was then added and the mixture was stirred at room temperature for an hour to decompose the ozonide. The mixture was then filtered and the precipitated product was washed with a small amount of methylene chloride to give N,N'-dimethanesulfonyloctahydro-1,5-diazocine-3,7-dione (0.94 g, 93%). mp XX ° C.; $^1$H NMR (DMSO-d$_6$) δ3.36 (s, 6H), δ4.18 (s, 8H); $^{13}$C NMR (DMSO-d$_6$)) δ38.7, δ59.1, δ206.5. LRMS (CI—NH3) calc. for C$_8$H$_{24}$N$_2$S$_2$O$_6$ 298: found m/z, 299, 316.

Oxidation of 1,5-di(p-toluenesulfonamido) diazacyclooctane-3,7-diols (3)

To a stirred solution of pyridine sulfur trioxide complex (0.882 g, 5.54 mmol) in DMSO (6.91 g, 88.5 mmol) containing triethylamine (0.828 g, 8.72 mmol) was added a stereoisomeric mixture of 1,5-di(4-toluenesulfonamido) diazacyclooctane-3,7-diols (0.200 g, 0.441 mmol) all at once. The resulting solution was stirred at room temperature for 1h, then poured over ice and extracted with ethyl acetate (4×10 mL). The combined organic layer was washed with water (5×10 mL), dried over MgSO$_4$, and concentrated in vacuum to give all oil which solidified on standing. Recrystallization from ethanol/hexane gave 0.410 g (41%) of 4 as a white solid mp 215°–217° C. $^1$H NMR (CDCl$_3$) δ2.42 (s, 6H), δ2.53 (d, 2H,d), δ2.88 (m, 2H), δ3.51 (d, J=11 Hz, 2H), δ3.71 (d, J=11 Hz, 2H), δ4.21 (m, 1H), δ7.69 (d, J=8.2 Hz, 4H), δ7.33 (d, J=8.2 Hz, 4H); $^{13}$C NMR (CDCl$_3$) δ21.6, δ46.1, δ55.3, δ68.8, δ90.4, δ128.1, δ129.9, δ132.1, δ144.2. LRMS (CI—NH$_3$) calc. for C$_{20}$H$_{24}$N$_2$S$_2$O$_6$ 452.0; found m/z, 452+1=453, 452 +18=470.

1,5-Dimethyl-3,7-diazabicyclooctane (5)

A suspension of 1,5-di(4-toluenesulfonamido)-3,7-bismethylenediazacyclooctane 1a (2.22 g, 4.98 mmol) in tetrahydrofuran (75 mL) containing lithium aluminum hydride (1.90 g, 50 mmol) was stirred under a nitrogen atmosphere for 42 h. The reaction mixture was quenched by the dropwise addition of 20% sodium hydroxide solution (4.5 mL) with external cooling. Stirring was continued at room temperature for 3 h and the white granular precipitate that formed was removed by filtration and washed with anhydrous ether (3×50 mL). The combined organic extracts were concentrated on a rotary evaporator to give 0.574 g (82%) of 5 as a colorless solid, mp XX° C. $^1$H NMR (CDCl$_3$) δ0.99 (s, 6H), δ2.71 (d, J=11.2 Hz, 4H), δ2.92 (d, J=11.2 Hz, 4H), δ2.61 (s, 2H. br); $^{13}$C NMR (CDCl$_3$) δ20.4, δ51.7, δ62.6. LRMS (EI) calc. for C$_8$H$_{16}$N$_2$ 140.1; found m/z, 140. Treatment of an ethanolic solution of 5 with picric acid afforded the picrate as a yellow solid, mp 258° C.

1,5-Dimethyl-3,7-diazabicyclooctane-d$_x$

In separate experiments a suspension of 1,5-di(4-toluenesulfonamido)-3,7-bismethylenediazacyclooctane 1a (0.223 g, 0.50 mmol) in tetrahydrofuran (50 mL) containing either lithium aluminum hydride (0.25 g, 6.6 mmol) or lithium aluminum deuteride (0.25 g, 6.0 mmol) was stirred under a nitrogen atmosphere for 42 h. The reaction mixture was quenched by the dropwise addition D$_2$O (1 mL) followed by 40% sodium hydroxide or 40% sodium deuteroxide solution (0.5 mL) with external cooling. Stirring was continued at room temperature for 5 h and the white granular precipitate that formed was removed by filtration and washed with anhydrous ether (3×50 mL). The combined organic extracts were concentrated on a rotary evaporator to give 0.052 g 0.057 g (82%) of 5 as a colorless solid, mp XX° C. The crude product was dissolved in benzene (25 mL) to which was added H$_2$O (3×1 mL) and the mixture was subjected to azeotropic distillation using a Dean Stark tube. Analysis of the product by Cl NH$_3$ MS showed:

Qi-130(LAD+D$_2$O+H$_2$O)m/z=142(C$_8$H$_{15}$DN$_2$)+1=142 $^{13}$C NMR (CDCl$_3$) δ20.2 (singlet), 20.0 (triplet, J=19.0 Hz)δ51.5, δ62.3.

Qi-128(LAH+D$_2$O+H$_2$O)m/z=142 (C$_8$H$_{15}$DN$_2$)+1=142 $^{13}$C NMR (CDCl$_3$) δ20.3 (singlet), 20.0 (triplet, J=19.0 Hz), δ51.5, δ62.3.

Qi-129 (LAD+D$_2$O+H$_2$O)m/z=143 (C$_8$H$_{14}$D$_2$N$_2$)+1=143 $^{13}$C NMR (CDCl$_3$) δ20.0 (triplet, J=19.2 Hz), δ51.5, δ62.1

$^1$H NMR (CDCl$_3$) δ0.99 (s, 6H), δ2.71 (d, J=11.2 Hz, 4H), δ2.92 (d, J=11.2 Hz, 4H), δ2.61 (s, 2H, br), $^{13}$C NMR (CDCl$_3$) δ20.4, δ51.7, δ62.6. LRMS (EI) calc. for C$_8$H$_{16}$N$_2$ 140.1; found m/z, 140.

A repeat experiment with 1,5-di(4-toluenesulfonamido)-3, 7-bismethylenediazacyclooctane 1a (0.446 g, 1.00 mmol) and lithium aluminum deuteride (0.427 g, 10.2 mmol) in tetrahydrofuran (50 mL) afforded 0.152 g of crude product. Analysis of this material by a DEPT experiment and its mass spectrum confirmed the presence of only one deterium atom and a CH$_2$D group. LRMS (EI) calc. for C$_8$H$_{15}$DN$_2$ 141.1; found m/z, ?

Stereoisomeric mixture of 1,5-di(4-toluenesulfonamido)diazacyclooctane-3,7-dione dioximes (9)

A suspension of 1,5-di(4-toluenesulfonamido) diazacyclooctane-3,7-dione 2a (0.900 g, 2.00 mmol), hydroxylamine hydrochloride (0.556 g, 8.00 mmol) and sodium acetate trihydrate (2.18 g, 16.0 mmol) in ethanol (70 mL) was heated with stirring under reflux for 5 d. The ethanol was removed on a rotary evaporator and the remaining residue was washed with water and dried over P$_2$O$_5$ in a vacuum dessicator to give 0.710 g (74%) of 6 as a colorless solid comprised of two geometric isomers.

A sample of crude 9 was recrystallized from ethanol to give the pure anti isomer 9b, mp 239° C.(d). $^1$H NMR (DMSO-d$_6$) δ2.41 (s, 6H), δ3.84 (s, 4H), δ4.09 (s, 4H), δ7.46 (d, J=7.9 Hz, 4H), δ7.69,(d, J=7.9 Hz, 4H), δ11.3 (s, 2H): $^{13}$C NMR (DMSO-d$_6$) δ21.0, δ47.0, δ52.3, δ126.6, δ130.0, δ134.6, δ143.9, δ152.9. LRMS (CI—NH$_3$) calc. for C$_{20}$H$_{24}$N$_4$S$_2$O$_6$ 480.1; found m/z 481,498.

N,N'-di(p-toluenesulfonyl)-1,3-dinitro-5,7-diaza-[3.3.0]-bicyclooctane (10) by oxidation of 9 with N-bromosuccinimide.

A mixture of sodium bicarbonate (7.4 g, 88.1 mmol), N-bromosuccinimide (6.6 g, 37.1 mmol), a stereoisomeric mixture of the dioximes 9 (3.5 g, 7.3 mmol) in 5% aqueous dioxane (200 mL) was stirred at room temperature for 4 days. The reaction mixture was partitioned between methylene chloride (150 mL) and 5% sodium hydroxide (150 mL) and the organic layer was separated. The aqueous layer was further extracted with methylene chloride (2×50 mL) and the combined organic layers were successively treated with 5% sodium hydroxide (2×50 mL), water (2×100 mL), brine and dried over Na$_2$SO$_4$. Concentration in vacuum gave a slightly yellow solid (2.06 g), most of which dissolved on treatment with acetone (70 mL). The acetone solution was concentrated in vacuum to give 10 as a slightly yellow crude product (1.89 g, 48%). Recrystallization from acetone /water gave crystalline needles of 10, mp 154°–156° C. $^1$H NMR (CDCl$_3$) δ2.47 (s, 6H), δ3.89 (d, J=11.5 Hz, 4H), δ4.00 (d, J=11.5 Hz, 4H), δ7.40 (d, J=8.3 Hz, 4H), δ7.70 (d, J=8.3 Hz, 4H); $^{13}$C NMR (CDCl$_3$) δ21.7, δ55.1, δ94.0, δ127.5, δ130.4, δ131.8, δ145.5. LRMS (CI-NH$_3$) calc. for C$_{20}$H$_{22}$N$_4$S$_2$O$_8$ 510.1; found m/z, XX

N,N'-di(4-toluenesulfonyl)-1,3-dinitro-5,7-diaza-[3.3.0]-bicyclooctane (10) by oxidation of 9 with m-CPBA A two-necked 50-ml round bottom flask equipped with condenser and a magnetic stirring bar was charged with urea (0.02 g, 0.3 mmol), disodium hydrogen phosphate (0.8 g, 5.6 mmol), the dioxime 9 (0.240 g, 0.5 mmol) and anhydrous acetonitrile (5 mL). After refluxing the mixture for 10 min, m-chloroperbenzoic acid (0.3 g, 1.8 mmol) was slowly added in 1 h. The suspension was refluxed for 2 h and then concentrated on a rotary evaporator at reduced presure. The residue was extracted with methylene chloride (3×20 mL). The combined extracts were washed with saturated sodium bicarbonate solution (4×15 mL), water (4×15 mL) and brine (2×30 mL). After drying over anhydrous sodium sulfate and cocentrating the solution on a rotary evaporator at reduced pressure compound 10 was obtained (0.064 g, 24%). The properties of 10 obtained in this experiment were identical with those exhibited by compound 10 isolated from the N-bromosuccinimide oxidation of 9.

Synthesis of N,N'-dinitro-1,3-dinitro--5,7-diaza-[3.3.0]-bicyclooctane (11) by nitrolysis of 10

Over a 2-min period 100% nitric acid (0.9 g, 14.2 mmol) was added to a stirred solution of trifluoroacetic anhydride (2.9 g, 14.1 mmol) in methylene chloride (10 mL) at −10° C. To this mixture, maintained at −10° C., a solution of 10 (0.36 g, 0.7 mmol) in methylene chloride (4 mL) was added over 0.5 h and stirring was continued for 2.5 h. The reaction mixture was poured onto ice-water (35 g) and the aqueous layer was extracted with methylene chloride (35 mL). The combined organic layers were washed successively with 5% sodium carbonate (50 mL), water (50 mL), and dried over sodium sulfate. Solvent removal gave a crude yellowish product (0.26 g) which was chromatographed on silica gel and eluted with acetone-hexane to give colorless crystals of 11 (0.060 g, 36%). mp 222°–224° C. $^1$H NMR (acetone-d$_6$) δ5.14 (d, J=13.9 Hz, 4H), δ4.99 (d, J=13.9 Hz, 4H); $^{13}$C NMR (acetone-d$_6$) δ56.6, δ94.0. LRMS (CI—NH$_3$) calc. for C$_6$H$_8$N$_6$O$_8$ 292.0; found m/z, XX

N,N'-dinitro-1,3-dinitro--5,7-diaza-[3.3.0]-bicyclooctane (11) from the nitrolysis of the dioxime of 1,5-diazacyclooctane-3,7-dione 9

To a refluxing solution of dioxime 6 (0.300 g, 0.6 mmol) in methylene chloride (50 mL), a solution of 98% nitric acid (5 mL) in methylene chloride (10 mL) containing catalytic quantities of urea and ammonium nitrate was added. After completing the addition the mixture was heated under reflux for 1 h. A blue-green color appeared initially and this changed to dark brown as the reaction progressed. The reaction mixture was cooled to room temperature and poured over ice. The layers were separated and the organic layer sea washed with water (50 mL) followed by saturated sodium bicarbonate solution (50 mL). The organic layer was dried over anhydrous magnesium sulfate and concentrated under reduced pressure. The residue was chromatographed on silica gel and eluted with acetone-hexane. The appropriate fractions were combined and recrystallized from acetone-hexane to give 8 (0.045 g, 25%) which was identical in all respects with the material isolated from the reaction of 7 with trifluoroacetyl nitrate.

1,5-Di-bromomethyl-3,7-diazabicyclooctane (7)

Figure 3B:
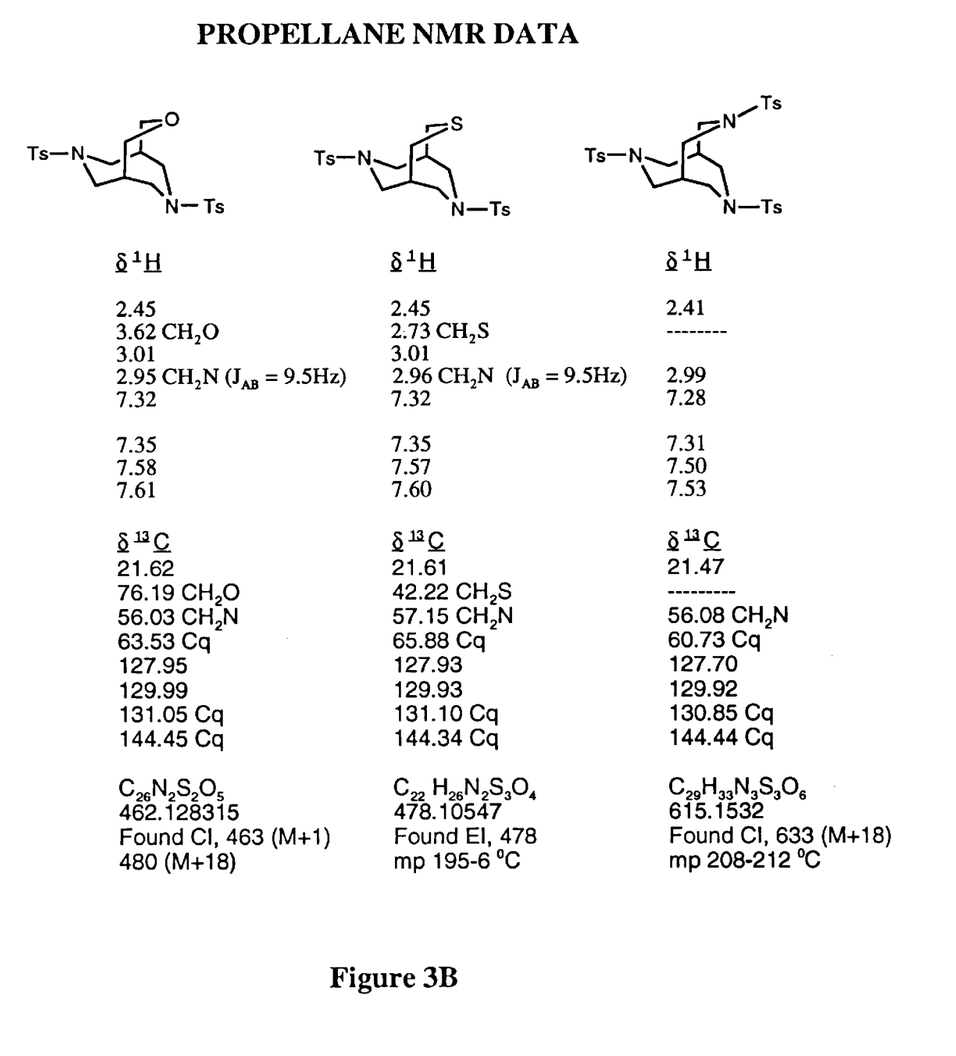
FIG. 3B illustrates the physical data for characterizing the several propellanes illustrated in FIG. 3.

To an ice-cooled (−5° to 0° C.) solution of 1,5-di(4-toluenesulfonamido)-3,7-bismethylenediazacyclo octane 1a (3.0 g, 6.7 mmol) in methylene chloride (250 mL) was added a solution of bromine (1.5 g, 9.3 mmol) in 70 mL over a five-hour period. The resulting yellow solution was washed successively with 5% sodium bicarbonate (150 mL), 5% sodium bisulfite (100 mL) and water (150 mL). The solution was dried over anhydrous sodium sulfate and the solvent was removed on a rotary evaporator to give 4.06 g (6.6 mmol, 99% yield of product. Recrystallization from acetone /water gave 2.69 g (4.3 mmol, 64% yield) of pur product, mp 218°–220° C. mp 218°–220° C.; $^1$H NMR (300 MHz, CDCl$_3$, TMS) δ2.45 (s, 6H), δ3.16 (d, J=10.5 Hz, 4H), δ3.31 (d, 10.5 Hz, 4H), δ7.33 (d, J=8.4 Hz, 4H), δ7.64 (d, J=8.3 Hz, 4H); $^{13}$C NMR (75 MHz, CDCl$_3$, TMS) δ21.6, δ34.0, δ56.0, δ57.3, δ127.7, δ130.0, δ131.9, δ144.5; LRMS (EI) calc. for C$_{22}$H$_{26}$N$_2$S$_2$O$_4$ 446.1; found m/z 445.9;

The propellanes as shown in FIG. 3A were prepared by the reaction of 3,7-dibromomethyl-1,5 ditosyldiazabicyclo octane with the appropriate ring closing agent. The reaction was conducted in DMSO at 125° C. The product was isolated by pouring the reaction mixture into water, extracting with an organic solvent and then concentrating. The heterocyclic propellane compounds of FIG. 3A were characterized and the data are prented in FIG. 3B.

An important aspect of the invention is that it provides a process for preparing the 3,7 disubstituted 1,5-diaza cyclooctanes. These are in effect the building blocks for the other compounds and processes. Generally, the procedure is to prepare 3,7 disubstituted-1,5 diazacyclooctanes having the aza nitrogen atoms substituted with carbonyl or sulfonyl groups. In the process, an ethylenically unsaturated compound is reacted with an amide or sulfonamide in solution and in the presence of a base to form the cyclooctane. The ethylenically unsaturated compound has two geminal substituents; at least one of which is a methylene attached to a halogen. The other may be the same or a methylene attached to a facile leaving group. The facile leaving group is a group which can readily be cleaved from the parent compound without materially changing the course of the reaction. A preferred group are carboxylic or sulfonic radicals attached by ester linkages to the methylene group. A particular series of such compounds are p-toluene sulfonate, methane sulfonate, acetate and pivalate. As shown in the prior examples, both gem substituents may be the methylene-halogen groups.

The invention provides the cyclooctanes, bicyclo octanes and propellanes and the functionalized derivatives as described above. Among the products of the invention are polymers having units of the 3,7 diaza bicyclo octane in the polymer chain. These units may be oriented through the aza nitrogen atoms in a 3,7 configuration or they may be oriented through the carbon atoms of in a 1,5 configuration. Also by having difunctional groups attached to the ring of the cyclooctane, bicyclo octane and propellane, the ring can be made pendant from the polymer chain. Such groups include ethylenically unsaturated groups as well as difunctional condensation reaction groups such as diamides.

Another group of products are the metal complexing compounds having complexing properties through the aza nitrogen atoms. In the 1,5 diaza bicyclic octanes and [m.3.3] diaza propellanes, the adjacent aza nitrogen rings are capable of acting as bi-dentate ligands to complex metals between the nitrogen atoms. The hydrogen substituted aza nitrogens are preferred for these situations. The bicyclic octane or propellane may be part of another structure such as a polymeric material and this would be suitable for removal of metal ions from water.

In the energetic materials of this invention, C-Nitro, N-Nitro and Fluoro amine groups are important substituents for the ring atoms because they increase the energy density of the parent compounds. Thus, a compound can have C-Nitro, N-Nitro and difluoro amine groups. For example, there can be two N-Nitro and two C-Nitro groups on the ring atoms. There can also be the mixture of the fluoro amine and nitro groups.

It is intended that the invention includes the equivalent compounds, products, reaction conditions, reaction steps, reaction processes and variations of such equivalents as are commonly practiced in this field as well as the specific embodiments described above.

We claim:

1. The compound 1,3,5,7-Tetranitro-3,7-Diazabicyclo [3.3.0] Octane.

* * * * *